United States Patent [19]

Jackowski

[11] Patent Number: 5,290,678
[45] Date of Patent: Mar. 1, 1994

[54] DIAGNOSTIC KIT FOR DIAGNOSING AND DISTINGUISHING CHEST PAIN IN EARLY ONSET THEREOF

[75] Inventor: George Jackowski, Halton Hills, Canada

[73] Assignee: Spectral Diagnostics Inc., Etobicoke, Canada

[21] Appl. No.: 695,381

[22] Filed: May 3, 1991

[30] Foreign Application Priority Data

Oct. 12, 1990 [CA] Canada .................. 2027434

[51] Int. Cl.⁵ ............... G01N 33/573; G01N 33/558
[52] U.S. Cl. .......................... 435/7.4; 422/56; 422/58; 435/7.94; 435/970; 435/973; 435/975; 436/514; 436/528; 436/530; 436/807; 436/808; 436/810
[58] Field of Search ............. 435/7.4, 7.9, 7.92, 435/7.94, 969, 970, 973, 975; 436/528, 530, 541, 808, 810, 811, 807, 514; 422/55, 56, 58, 60, 61

[56] References Cited

U.S. PATENT DOCUMENTS

| | | | |
|---|---|---|---|
| 4,857,453 | 8/1989 | Ullman et al. | 436/810 X |
| 5,037,736 | 8/1991 | Freitag et al. | 435/7.9 |
| 5,071,746 | 12/1991 | Wilk et al. | 435/7.94 |
| 5,087,556 | 2/1992 | Ertinghausen | 435/7.9 |

FOREIGN PATENT DOCUMENTS

| | | |
|---|---|---|
| 384130 | 8/1990 | European Pat. Off. |
| WO9101498 | 2/1991 | PCT Int'l Appl. |
| 9101498 | 2/1991 | PCT Int'l Appl. |

OTHER PUBLICATIONS

E. Hoberg, H. A. Katus, K. W. Diederich and W. Kubler, Myoglobin, creatine kinase-B isoenzyme, and myosin light chain release in patients with unstable angina pectoris, European Heart Journal (1987), pp. 990-994.

Speicher et al., "Cardiovascular Subproblems", in *Choosing Effective Laboratory Tests*, W. B. Saunders Co., Philadelphia (1983), pp. 155-163.

Reese et al., *CMA Journal*, vol. 124, (1981), pp. 1585-1588.

Katus et al., *Am. J. Cardiology*, vol. 54, (1984), pp. 964-970.

Scan. J. Clin Lab. Invest., vol. 44, 1984, pp. 679-682-Baadsgaard & Schmidt.

Katus et al., *am. J. Cardiol.*, vol. 21, (1989), pp. 1349-1353.

Cummins et al., *Am. Heart J.*, vol. 113, No. 6, (1987), pp. 1333-1344.

*Primary Examiner*—Esther L. Kepplinger
*Assistant Examiner*—Susan C. Wolski
*Attorney, Agent, or Firm*—Cushman, Darby & Cushman

[57] ABSTRACT

A diagnostic test kit is disclosed for assessing whether patient chest pain is cardiac in origin and for differentiating between unstable angina and myocardial infarction at early onset of patient chest pain. The test kit comprises a receptacle for receiving and retaining a sample of blood or serum of the patient and at least three monoclonal or polyclonal antibodies suspended on a carrier. Each antibody is complementary to a different protein released by the heart muscle during early stages of a myocardial infarction and has corresponding reagents which are independently responsive to each antibody reacting the complementary protein. The combined response of reagents indicates the diagnostic condition of the patient.

2 Claims, 5 Drawing Sheets

CK, CK-MB

MYOGLOBIN

MLC

TROPONIN I

TROPONIN T

MHC

TROPOMYOSIN

DIAGNOSTIC KIT FOR DIAGNOSING AND DISTINGUISHING CHEST PAIN IN EARLY ONSET THEREOF

FIELD OF INVENTION

This invention relates to a novel one-step diagnostic test in the form of a panel which is used as a method of providing an accurate, simple, rapid, and portable diagnosis for assessing whether patient chest pain is cardiac in origin and for differentiating between unstable angina and myocardial infarction ("MI") at early onset of patient chest pain. In particular, the panel test will simultaneously assess the serum or plasma levels of three different substances or markers found in serum or plasma during or after cardiac damage, utilizing an enzyme immunoassay sandwich dry chemistry format. In the preferred embodiment of the invention, the three markers are creatine kinase (CK), myoglobin, and myosin light chains (MLC).

BACKGROUND OF THE INVENTION

Emergency diagnosis of myocardial infarction has depended on physician acuity, and an assessment of a patient's symptoms, such as chest pain or pressure, possibly radiating down the arm and up the neck, fatigue, sense of impending doom, shortness of breath, pallor, cold clammy skin, peripheral cyanosis or rapid thready pulse.

Most North American patients experiencing chest pain will report to a doctor or emergency room within six (6) hours after the onset of the chest pain. It is therefore essential that a diagnostic test be effective in the early stages of an MI.

Several cardiac tests have been used to detect MI. These tests include: ECG, SGOT/AST, LDH, CK-MB Immunoassay and NA Latex Myoglobin Particle Enhanced Assay. However, there are no single enzyme cardiac test which enables the emergency department physician to identify the source of chest pain as cardiac or non-cardiac. Further, it is only after a myocardial infarction has been confirmed may thrombolytic therapy be initiated. The earlier such therapy is initiated, the greater likelihood of full recovery of the patient or at least minimization of cardiac damage. It is therefore essential for a physician to identify the pain as cardiac or non cardiac.

The electrocardiogram (ECG) may be used to detect an MI. However ECG is not diagnostic until after the heart has suffered severe damage. The diagnostic specificity of the ECG is only 51% in the initial phases of chest pain. Therefore, ECG is not suitable for early detection of MI.

Serum glutamic oxalacetic transaminase/aspartate transferase (SGOT/AST) is a predominant enzyme found in high concentration in heart muscle. Serum tests to determine levels of SGOT are used in diagnosing myocardial infarction. However, SGOT only begins to rise about 8-10 hours following the onset of chest pain, peaks within 24-36 hours and returns to normal after 5-7 days. SGOT is not particularly helpful in diagnosing myocardial infarction in an emergency setting at an early stage of patient chest pain. Also, SGOT is not specific to cardiac muscle. It is found in many tissues including skeletal muscle, liver and kidney, being released as a result of intra muscular injections, shock, during liver disease, and hepatic congestion, and is therefore of little value in detecting specific cardiac tissue injury.

Lactate Dehydrogenase (LDH) is an enzyme found in high concentration in many tissues, including heart, skeletal muscle and liver. Tests to detect the presence of LDH in serum are used to diagnose myocardial infarction. There are five common isotypes of which the heart contains predominantly LDH1 and LDH2. LDH levels begin to rise 24-36 hours after the onset of chest pain, and peak after 48-72 hours, returning to normal after 4-8 days. LDH is therefore not useful as an indicia of MI at an early stage of patient chest pain. In addition, LDH is not specific to cardiac damage, and appears with pulmonary embolism, haemolysis, hepatic congestion, renal disease and skeletal muscle damage. This lack of specificity also decreases the utility of LDH as a diagnostic aid.

Creatine kinase (CK) is an enzyme found in muscle tissue. CK catalyses the conversion of creatine and adenosine triphosphate (ATP) to phosphocreatine and adenosine diphosphate (ADP). One of several CK isoenzymes is CK-MB which is found in cardiac tissue. CK-MB is a sensitive marker for the detection of myocardial infarction, as it is released from damaged myocardium tissue. CK-MB thereafter is present in the serum of an affected individual. FIG. 1 illustrates the concentration of CK in the serum of a patient as a function of time. (ref. Lee T. H. et al. (1986) Ann. Intern. Med. 105, 221-233)

The CK-MB immunoassay is the standard diagnostic test for myocardial infarction. A method describing the use of CK-MB is disclosed in U.S. Pat. No. 4,900,662 entitled "CK-MM Myocardial Infarction Immunoassay".

Shah, U.S. Pat. No. 4,900,662 discloses a method for determining the initial elevated concentration level of CK-MM-a, an isoform of CK-MM, and CK-MM-a and CK-MM-b concurrently in patient serum following a myocardial infarction. Use of the method provides an accurate estimation of the time of the infarction. The method involves determining the combined concentration of CK-MM-a and CK-MM-b and the concentration of CK-MM-a in serum, in order to determine the time of the acute phase of myocardial infarction. Reagents are disclosed and comprise novel polyclonal and monoclonal antibodies for CK-MM-a which do not bind significantly with CK-MB, CK-MM-b or CK-MM-c, an anti-CK-MM-b antibody which does not bind significantly with CK-MB, CK-MM-a or CK-MM-c, an anti-CK-MM-a+b antibody which binds with CK-MM-a and CK-MM-b but does not bind significantly with CK-MB or CK-MM-c, labelled derivatives of these antibodies, insoluble supports to which these antibodies are adhered, and kits containing one or more of these reagents. Enzyme labelled and radiolabelled CK reagents are particularly useful.

There are difficulties with the use of CK-MB alone as a diagnostic marker. First, serum levels of CK-MB are not elevated until 6-8 hours after the onset of myocardial infarction, and do not peak until after 12 hours, making early emergency diagnosis and treatment difficult.

Secondly, the CK-MB test must be conducted in a laboratory by trained laboratory technicians. In non-urban locations, it may not be feasible to have the test conducted and the results interpreted expeditiously, resulting in increased delay in diagnosis and hence increased costs to the health care system in terms of hospitalization costs of a patient awaiting diagnosis.

Thirdly, CK-MB has been located in normal skeletal muscle tissue, consequently rendering the test less cardiac specific, and the diagnosis less certain.

Myoglobin is another protein located near the skeletal or myocardial cell membrane. It is expelled from the cell as soon as the cell membrane becomes abnormally permeable, for example, during myocardial ischemia, a reversible state. Myoglobin is detectable in the serum within 1.5 hours of the onset of chest pain. The medical research community believes that myoglobin is released by myocardial necrosis, and it is therefore a useful early marker of myocardial injury. FIG. 2 illustrates the concentration of myoglobin in the serum as a function of time. (ref. Grenadier E. et al. (1981) Am. Heart J. 105, 408–416; Seguin J. et al. (1988) J. Thorac. Cardiovasc. Surg. 95, 294–297)

In determining the origin of chest pain, an acute myocardial infarction can be excluded if no elevation of serum myoglobin is detected within 2–3 hours after the onset of pain.

An NA Latex Myoglobin Particle Enhanced Assay is a commercially available assay kit for the detection of myoglobin. The assay is based on the reaction between antigen present in human body fluids and antimyoglobin antibodies covalently coupled to polystyrene particles. The sample, N Myoglobin Reagent, a solution for the elimination of nonspecific reactions and N Reaction Buffer are pipetted automatically into a cuvette. Light scattering is measured by a nephelometric procedure after 12 minutes of incubation time and the myoglobin concentration is calculated from a calibration curve.

Myoglobin may also be assayed using a radioimmunoassay but there is no enzyme-linked immunosorbent assay (ELISA) format yet available.

There are difficulties with the use of myoglobin alone as a diagnostic marker. Myoglobin does not indicate a particular type of myocardial injury, such as myocardial infarction. Myoglobin can also be present during such diverse conditions as shock, renal disease, rhabdomyolysis, and myopathies. Additionally, myoglobin concentrations in serum and plasma generally depend on age and sex and vary over a wide range in normal healthy humans. Serum concentrations up to 90 ug/l are generally regarded as the upper limit of the reference range for healthy people. Therefore, what may be a normal level for one individual may be indicative of a serious problem in another individual, making diagnosis somewhat less accurate than would be desirable.

Myosin light chains (MLC) are integral parts of the myosin myofibril, but their functional role is still unclear. MLCs exist in slow, fast, atrial, and ventricular muscles. It is known that MLCs are highly sensitive for myocardial ischemia. MLCs appear in the serum rapidly, and their levels remain elevated for up to 10 days following myocardial necrosis. FIG. 3 illustrates the concentration of MLC in patient serum as a function of time. (ref. Wang J. et al. (1989) Clin. Chimica. Acta 181, 325–336; Jackowski G., Symmes J. C. et al. (1989) Circulation Suppl. 11 80, 355.) MLC also has prognostic value in determining the success of thrombolytic therapy. Higher levels of MLC, indicate a worse prognosis, and also corresponds to a larger infarction. Falling levels over several days indicate a tendency towards patient recovery, whereas spiking or stadico pattern indicate a tendency towards infarction and a need for intervention.

There are two principal types of MLC known as MLC1 and MLC2, which exist as a soluble pool in the myocardial cell cytoplasm and also integral with the myosin myofibril. In the ventricular muscle, MLC2, and perhaps MLC1, is identical with the isotype expressed in slow skeletal muscle. MLC1 is elevated in 80-85% of the patients with cardiac pain. MLC1 is a very sensitive indicator of unstable angina and coronary heart disease.

Other cardiac markers, low molecular weight cardiac proteins (LMWCP) may be used as cardiac markers. Examples of such cardiac markers include components of the contractile apparatus, namely, troponin, including troponin-T, troponin-I and troponin C, mitochondrial enzymes, such as triose P isomerase, low molecular weight polypeptides which are readily released from the heart, and sarcolemmal membrane proteins or protein fragments which may be released early after the onset of ischemia, in particular, a 15 kd sarcolemma protein and a 100 kd complex glycoprotein which are cardiac specific.

The cardiac isotype troponin-I inhibits the interaction between actin and myosin molecules during rest periods between contractions of the heart muscle. Troponin-I appears in serum of patient within 4–6 hours after MI and remains elevated for 7–8 days. FIG. 4 illustrates the concentration of troponin-I as a function of time. (ref. Cummins B., Auckland M. L. and Cummins P. (1987) Am. Heart J. 113, 1333–1344.). It is cardiac specific and has a greater sensitivity than other markers in detecting cardiac versus skeletal muscle injury.

Troponin-T is part of the troponin-tropomyosin complex of the thin filament and serves as a link between the tropomyosin backbone and the troponin-I troponin C complex. Troponin-T is a basic protein and has isotypes in cardiac and fast and slow skeletal muscles. It appears in serum within 3 hours and remains elevated for at least 10 days following MI. FIG. 5 illustrates the concentration of troponin-T as a function of time. (ref. Katus H. A. et al. (1989) J. Mol. Cell Cardiol. 21, 1349–1353.). Troponin-T follows a biphasic release pattern. It is cardiac specific and very sensitive for MI.

Myosin heavy chains (MHC), and tropomyosin, are heavier molecular weight proteins which may also be used as cardiac markers. MHC is part of the major contractile protein of muscle. Fragments of MHC can be released from the ventricule into serum after myocardial cell necrosis and subsequent irreversible membrane injury. Although MHC fragments do not appear quickly in the serum following myocardial cell necrosis, MHCs remain elevated for at least 10 days following MI, and peak levels of MHC are observed 4 days after MI. FIG. 6 illustrates the concentration of MHC as a function of time. (ref. Leger J. O. C. et al. (1985) Eur. J. of Clin. Invet. 15, 422–429, Seguin J. R. et al. (1989) J Thorac. Cardiovasc. Surg. 98, 397–401.). The area under the MHC release curve correlates very well with the extent of myocardial cell damage. However, MHC levels are of little clinical value during the acute phase of MI.

Tropomyosin is a dimer formed from two polypeptide which are part of the regulatory system in muscle contraction. Tropomyosin is detectable in serum approximately 7–8 hours after myocardial infarction, and like CK-MB, is very sensitive for myocardial infarction. FIG. 7 illustrates the concentration of tropomyosin as a function of time. (ref. Cummins P. et al. (1981) Clin. Sci. 60, 251–259). However, tropomyosin is not cardiac specific since it is elevated in conditions of skeletal muscle trauma.

There are limitations for each of the current standard diagnostic methods for myocardial infarction. None provide a highly sensitive, specific, rapid, and simple diagnostic test which may be conducted soon after the onset of chest pain, for example, in an ambulance or doctor's office.

The present invention combines and measures at least three different markers of cardiac damage present in the blood or serum of a patient in early onset of chest pain in order to provide an improved method of diagnosis of myocardial infarction for use in the early stages of unstable angina or MI.

SUMMARY OF THE INVENTION

The disadvantages of the prior art may be overcome by providing a one-step, accurate, rapid, and portable panel diagnostic test to be used in emergency settings to detect the presence of at least three markers of cardiac damage in a patient's serum. The test results will determine whether the patient is suffering from unstable angina or whether a myocardial infarction has taken place. Early detection of MI enables thrombolytic therapy to be commenced at an early stage. Cardiac damage will therefore be minimized, and the patient's chance of survival will be increased. The results of the panel test will distinguish between unstable angina and myocardial infarction, even up to several days following the onset of pain. The panel test will utilize an enzyme immunoassay sandwich dry chemistry format. Serial temporal measurements with the panel will offer prognostic information to the physician as to the extent of muscle damage and the success of thrombolytic intervention. In the preferred embodiment of the invention, the three markers are creatine kinase (CK), myoglobin, and myosin light chains (MLC).

According to one aspect of the invention there is provided a diagnostic test kit for detecting a myocardial infarction at early onset of patient chest pain. The test kit comprises a receptacle for receiving and retaining a sample of blood or serum of the patient and a detection means for communicating with the sample. The detection means comprises at least three monoclonal or polyclonal antibodies suspended on a carrier, each antibody being complementary to a different protein released by the heart muscle during early stages of a myocardial infarction, and corresponding reagents which are independently responsive to each antibody reacting with the complementary protein. The combined responses of reagents indicates the diagnostic condition of the patient.

In drawings which illustrate the embodiments of the invention,

DETAILED DESCRIPTION OF THE INVENTION

Figure 8:
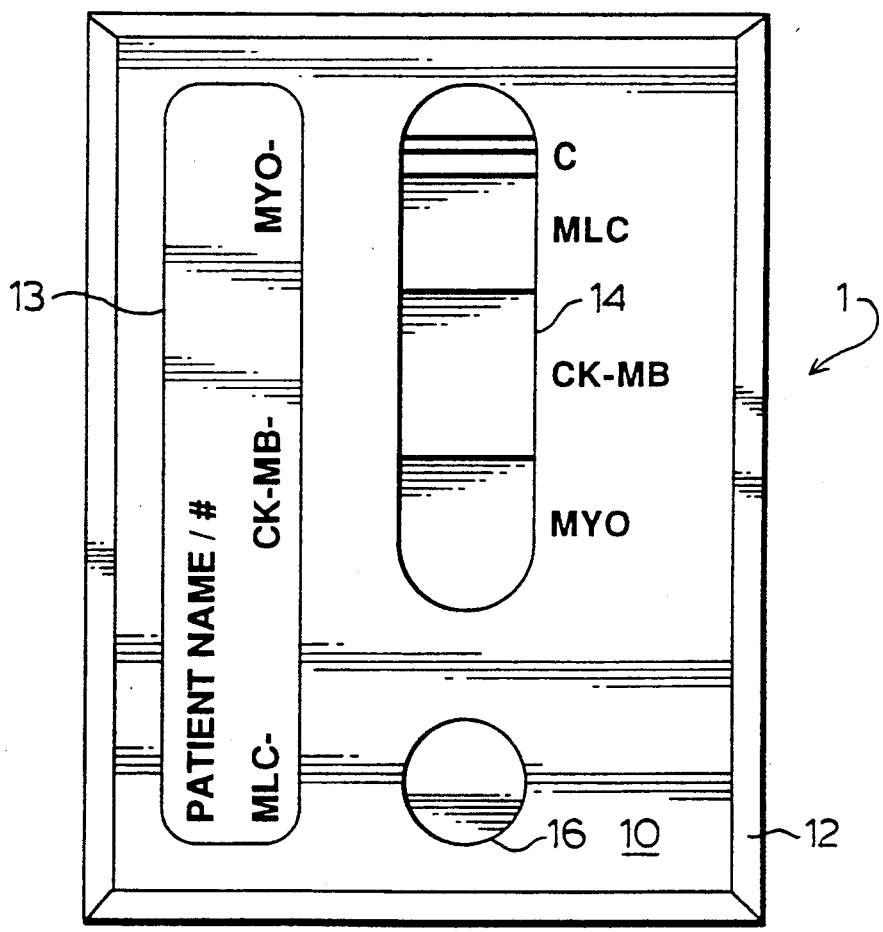
FIG. 8 is a plan view of the preferred embodiment.
Figure 9:
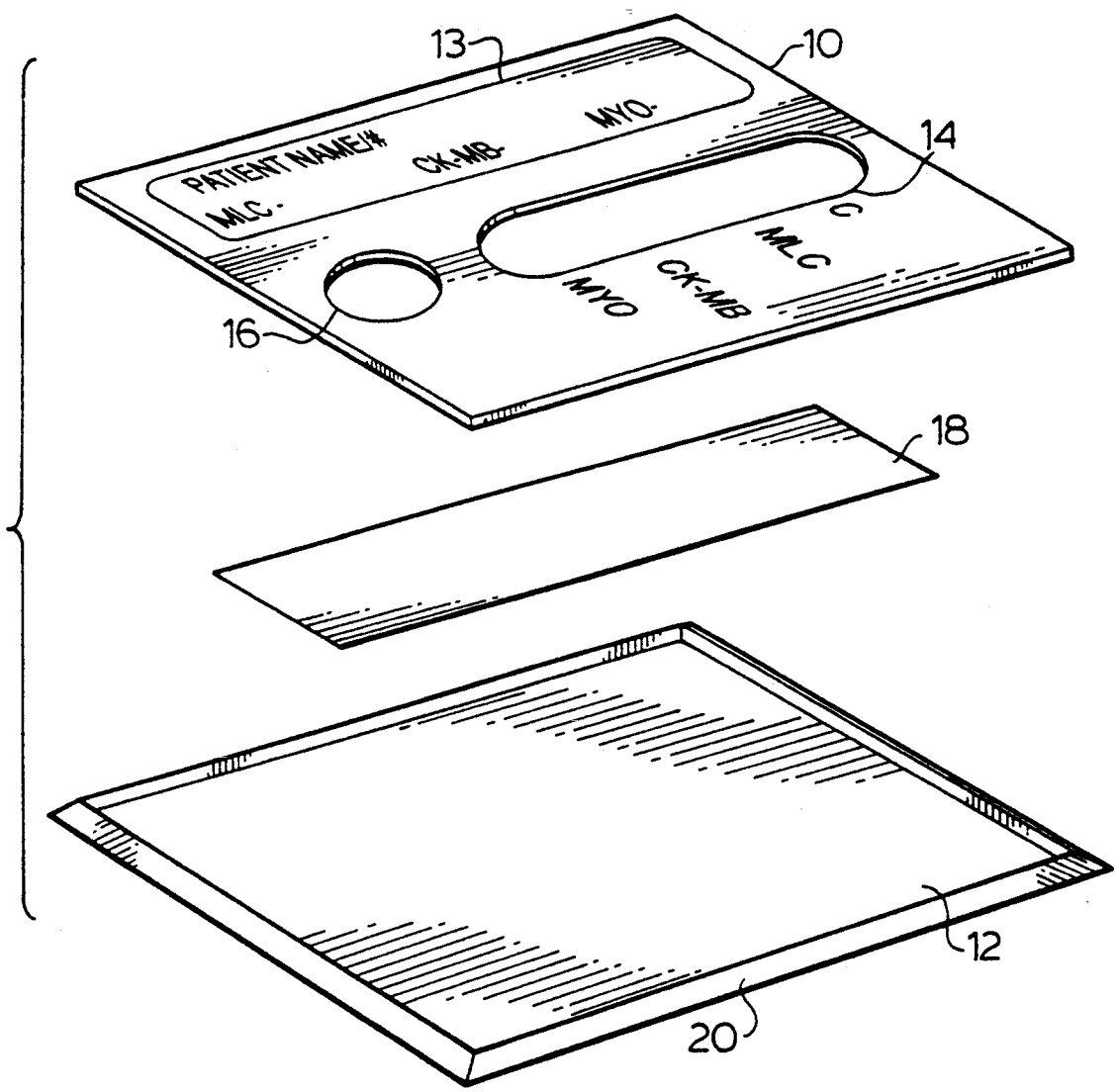
FIG. 9 is an exploded perspective view of the embodiment of FIG. 8.

The invention is generally illustrated in FIG. 8. In the preferred embodiment the invention is in a panel format identified as 1.

The panel format to be used is known and is commercially available. The panel format is similar to a format currently being used in association with pregnancy testing and is commercially available under the trademark BIOSIGN.

Figure 1:
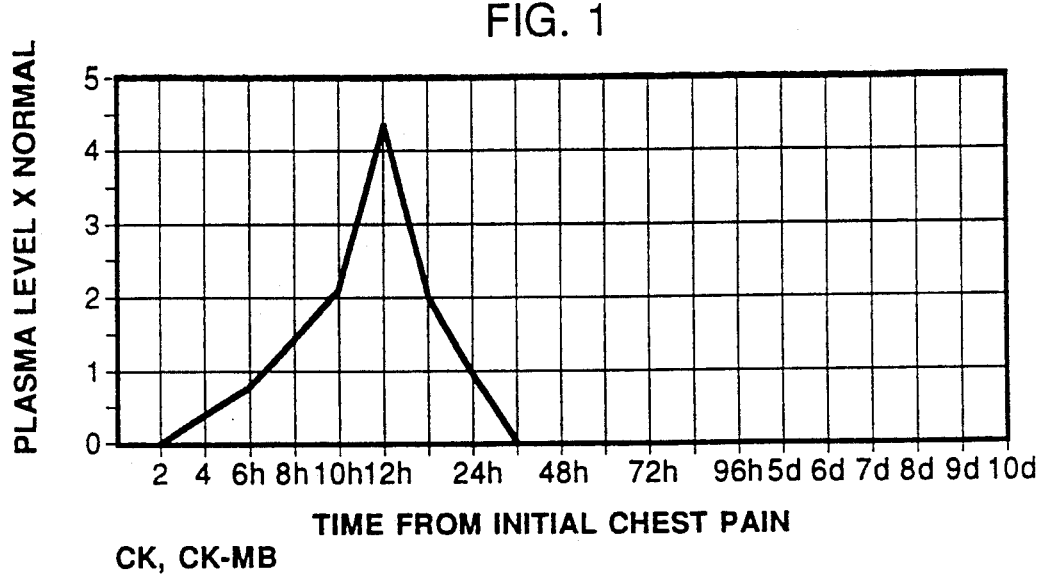
FIG. 1 is a graph illustrating the level of CK in serum as a function of time.

The panel consists of a polypropylene card having a front panel 10 and a back panel 12. Front panel 10 has a display window 14, one for each cardiac marker and a sample window 16, as illustrated in FIG. 1. Underneath front panel 10 is an exposed dry chemistry membrane 18 which is affixed to the back of front panel 10 by suitable means. Back panel 12 is provided with a lip 20 which extends around the perimeter of back panel 12 for receiving front panel 10 in a snap fit thereby sealing the membrane 18 between the front and back panel.

While the front and back panel have been described as being snapped together, there are numerous other suitable methods of joining the two together which would be apparent to a person skilled in the art.

Front panel 10 may also be provided with an area 13 upon which the patient's name or identification may be written. Also space may be available to write the results of the test.

Figure 10:
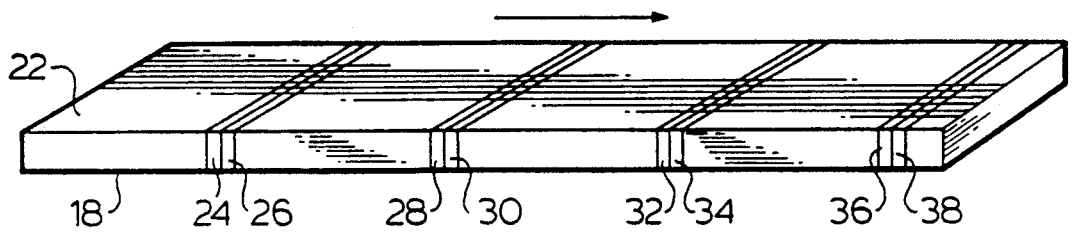
FIG. 10 is an oblique view of the membrane of the embodiment of FIG. 8.
Figure 11:
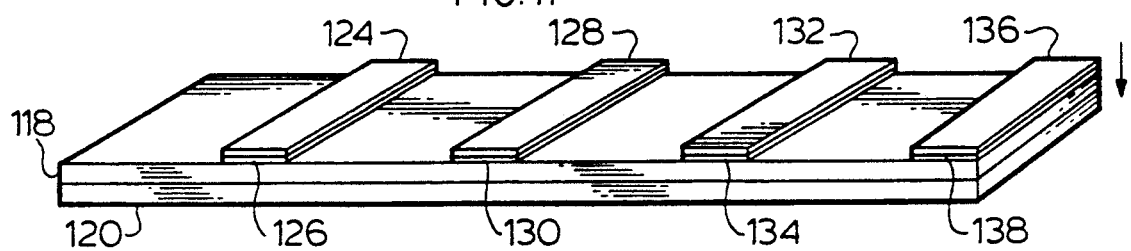
FIG. 11 is an oblique view of a second embodiment of the membrane.

With reference to FIG. 10, membrane 18 is the carrier of the monoclonal or polyclonal antibodies. In the preferred embodiment, the flow of blood or serum is from one end to the other end as shown by the arrow. End 22 is aligned with sample window 16. An immobilized captured antibody 26 is layered against or bonded to an antibody-enzyme conjugate 24 which is directed against a different epitope on the antigen than that which is recognized by the antibody 26. Antibody 26 is complementary to the myosin protein. Similarly, antibody 30 is layered with a corresponding reagent 28. Antibody 30 is complementary to CK-MB. Likewise, antibody 34 is layered with a reagent 32. Antibody 38 is complementary with the myosin light chain. Antibody 38 is one which is complementary to any protein found in normal serum or blood. Antibody 38 is layered with reagent 36.

The monoclonal and polyclonal antibodies can be prepared by using conventional procedures with any mammal used for polyclonal antibody production.

In the preferred embodiment, a labelled reagent is used. The antibody reagent is labelled or chemically bonded to a distinctive moiety which can be observed or measured to verify or quantify the presence of an analyte in the serum or blood or on the dry chemistry membrane. Ligands and groups which can be conjugated to the antibodies of this invention for use as a diagnostic tool include elements, compounds or biological materials which have physical or chemical characteristics which can be used to distinguish the antibodies to which they are bonded from other antibodies.

At least two antibodies of the type mono/poly or rabbit/poly, goat/poly per cardiac marker are required.

The antibodies are affinity purified against their specific cardiac immunogen and then further purified by cross-adsorption against a non-related species to eliminate nonspecific specific immunoglobulins.

In use, the diagnostician, for example a physician, ambulance attendant or nurse, adds three drops or less than 100 μl of the patient's serum or blood to the sample window 16. The sample will migrate along the membrane 18 by capillary action and will successively come into contact with the antibody and reagent pairs 24 and 26, 28 and 30, 32 and 34 and 36 and 38.

The specific cardiac marker if present in the sample binds to the antibody immobilized on the membrane. The corresponding reagent will also react and is visualized by a change in colour. The colour change is proportional to the concentration of the marker in the sample. Therefore if the test kit is used in timed intervals the increase or decrease in marker concentration can also be determined and used as a diagnostic tool. The results of the test should be completed within 3-5 minutes.

In the preferred embodiment, a blue band will show for each cardiac marker which is present in the sample. The intensity of the band is quantifiable using a reflectometer, which relates the colour intensity to the concentration level of a particular marker. The reflectometer may contain a microprocessor, so that the quantified result for each cardiac marker being tested in the panel may be produced and printed out as a concentration of each marker along with the patient's name or identification.

The test preferably is sensitive to marker concentrations from 0.5 ng/ml to 25 ng/ml using 3 drops or less than 100 ul of serum or plasma with a within run and between run precision coefficient of variation of less than 15%.

The cardiac markers utilized in the test will depend on the properties of those markers. In the preferred embodiment, there will be a panel having myoglobin, MLC, and CK-MB, as illustrated in FIG. 8.

Myoglobin is released very early from the myocardial cell, is not cardiac specific, has a very high sensitivity for myocardial infarction and necrosis and is not released by anoxic injury in the absence of necrosis. MLC is cardiac specific, and permits differentiation of cardiac from non cardiac pain, and is released early but not as early as myoglobin. CK-MB differentiates angina from myocardial infarction, but is not detectable until approximately six hours after the onset of chest pain and therefore is not of use alone as an emergency diagnostic test.

Figure 2:
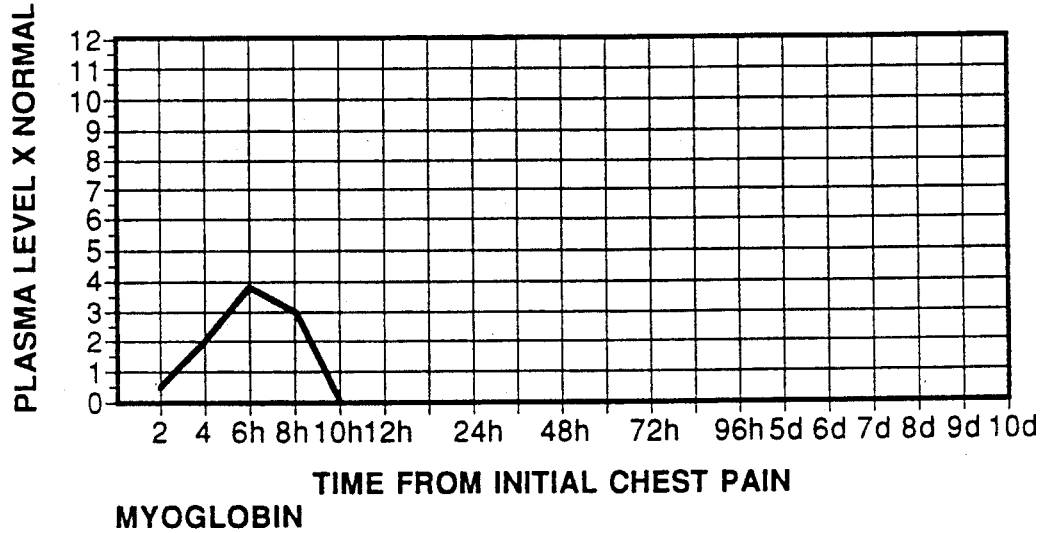
FIG. 2 is a graph illustrating the level of myoglobin in serum as a function of time.
Figure 3:
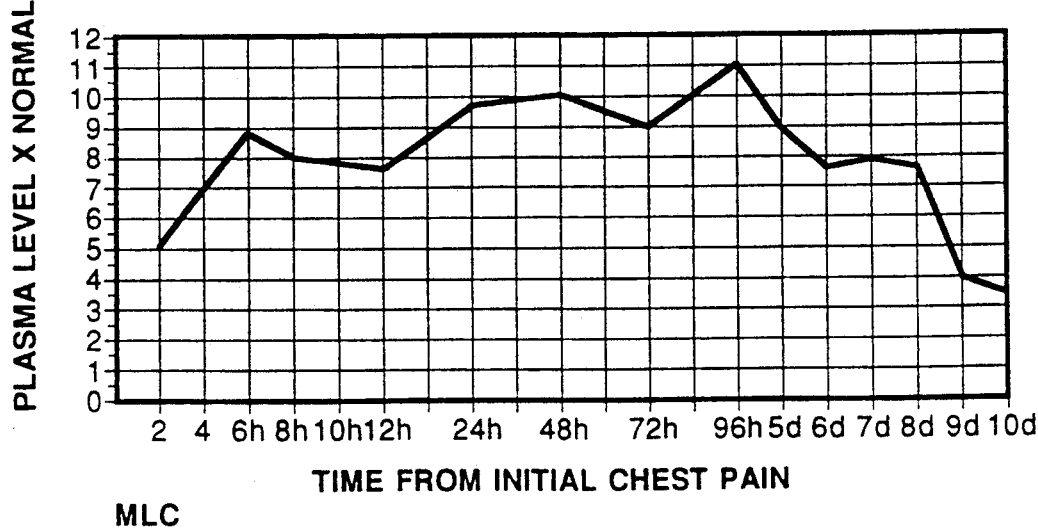
FIG. 3 is a graph illustrating the level of MLC in serum as a function of time.
Figure 4:
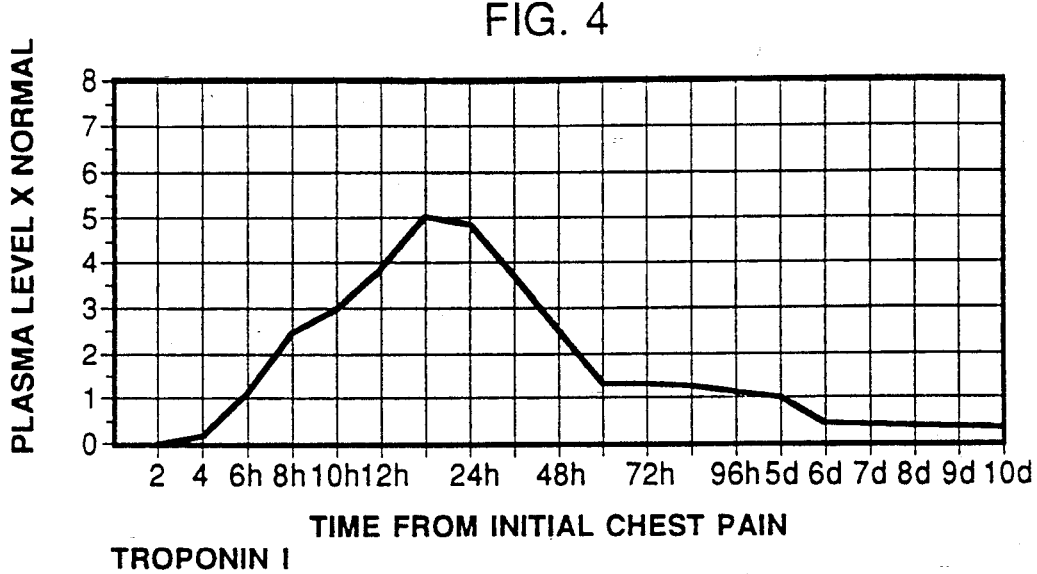
FIG. 4 is a graph illustrating the level of troponin-I in serum as a function of time.
Figure 5:
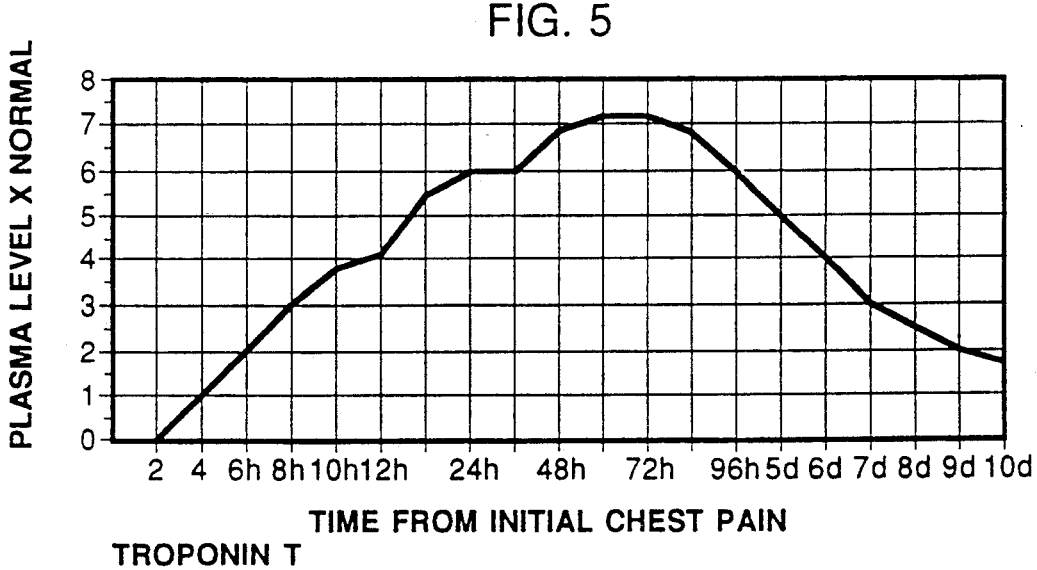
FIG. 5 is a graph illustrating the level of troponin-T in serum as a function of time.
Figure 6:
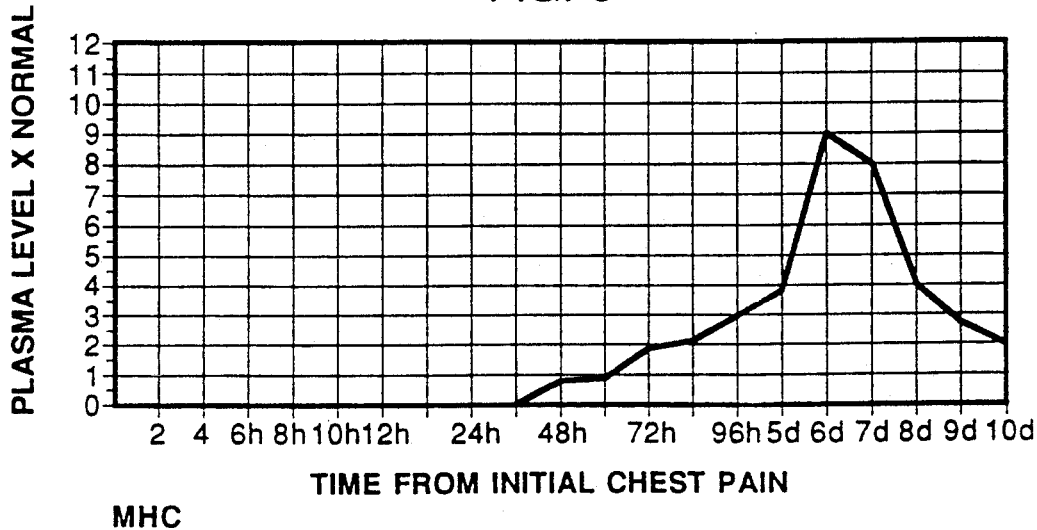
FIG. 6 is a graph illustrating the level of MHC in serum as a function of time.
Figure 7:
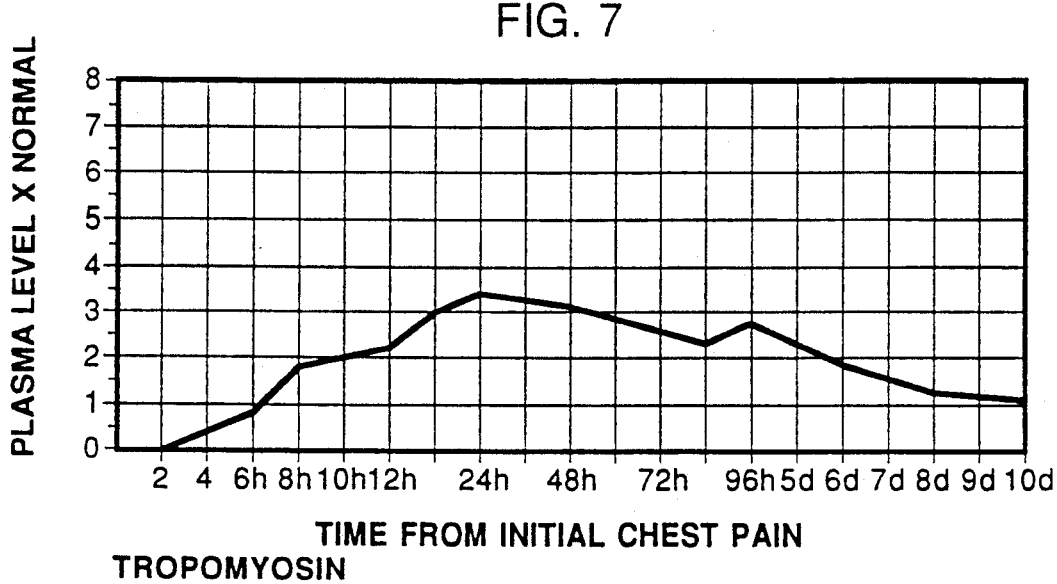
FIG. 7 is a graph illustrating the level of tropomyosin in serum as a function of time.

Referring to FIGS. 1, 2 and 3 and if the three cardiac markers to be used are CK-MB, myoglobin, and MLC, the following interpretation of the results would provide a diagnosis.

If the panel shows positive for MLC and negative for myoglobin and CK-MB, it would indicate that the patient's chest pain is cardiac and that the source is unstable angina.

If myoglobin and MLC are positive and CK-MB is negative it would indicate an early evolving myocardial infarction and intervention therapy could be initiated.

If all three are positive, it would indicate a myocardial infarction.

If MLC and CK-MB are positive and myoglobin is negative, it would indicate a myocardial infarction.

If myoglobin and CK-MB are positive and MLC is negative, the patient could have skeletal muscle trauma (a false positive) or be in the midst of a myocardial infarction.

The test could not distinguish between a false positive and a "small" myocardial infarction in this case, as the MLC release curve has slight dips at several intervals and the patient may have a small subendocardial infarction and be tested at the time of a "dip". When the infarct is small, the "dip" is down to almost normal levels, and therefore the patient would test negative for MLC. Positive diagnosis would rely on the presence of CK-MB.

In the event that the patient is having a large myocardial infarction, the "dip" in MLC levels will not be so large as to be the same as normal levels, and therefore, MLC will remain detectable.

In other embodiments, the test panel may utilize different combinations of antibodies in the same format, such that different cardiac markers are assessed. In order to ensure that the panel will detect cardiac tissue damage at an early stage of patient chest pain, it is necessary to utilize at least one antibody corresponding to a marker which is present in large quantities at an early stage of cardiac damage, such as CK, myosin light chains or myoglobin. Low molecular weight cardiac proteins having the characteristics and properties of CK, myosin light chains or myoglobin may also be used in the kit.

Suitable proteins and enzymes may be selected from the following: troponin, including troponin-I, troponin C, troponin-T and sarcolemmal membrane proteins, triose P isomerase or any heavy molecular weight cardiac proteins having the characteristics and properties of creatine kinase, myoglobin or myosin light chains.

Other proteins such as tropomyosin, and myosin heavy chains may also be added to the kit. The kit would then be able to detect MI if the patient arrives for diagnosis many hours after onset of chest pain where the patient is in the later stages of MI.

In a second embodiment, membrane 18 may have a layer of captured antibody 126 and a corresponding reagent 124. Similarly for each other marker to be detected, a corresponding pair of antibodies and reagents are provided, i.e. 128 and 130, 132 and 134 and control pair 136 and 138. In use, the sample is dropped onto each pair and the results are read in the same manner as described above.

The dry chemistry membrane 118 can be supported by absorbent material 120. Absorbent material 120 will enhance the draw of the serum through the membrane.

A further embodiment for the test kit is to use a blood sample tube which is commonly used to draw blood samples from patients. The inside wall of the tube could act as a carrier for the monoclonal and polyclonal antibodies and reagents. After the sample is drawn from the patient, the user simply shakes the tube so that the antibody reacts with the blood. Colour changes as described above will take place if the cardiac protein is present in the blood.

Although the disclosure describes and illustrates preferred embodiments of the invention, it is to be understood that the invention is not limited to these particular embodiments. Many variations and modifications will now occur to those skilled in the art. For a definition of the invention, reference is to be made to the appended claims.

The embodiments of the invention in which an exclusive property of privilege is claimed are defined as follows:

1. A diagnostic test kit for rapidly diagnosing the cause of chest pain of a patient in the early onset thereof, said kit comprising
   a front panel comprising a sample window and a display window, the sample window to receive a sample of serum or plasma from said patient;
   a back panel; and
   a dry chemistry membrane affixed between the front and back panels positioned for display in at least the display window,
   wherein, said membrane comprises:
   a sample region and a control region, said sample region positioned to receive the sample from the sample window; and
   at least three antibody pairs located at discrete locations along said membrane between the sample region and the control region, each of said antibody pairs comprising an antibody reagent member and an immobilized capture antibody member, each capture antibody member being located on said membrane closer to the control region than the corresponding antibody reagent member, each antibody pair having a measurable or observable moiety labelled or chemically bonded to the antibody reagent member of each said antibody pairs,
   the antibody pairs being monoclonal or polyclonal and comprising:
   a first antibody pair that specifically binds to myoglobin,
   a second antibody pair that specifically bind to myosin light chains, and
   a third antibody pair that specifically binds to at least one protein selected from the group consisting of CK-MB, troponin I, and troponin T,
   such that upon adding sample to the sample window, analytes present in the sample and complementary to the antibody pairs will migrate toward the control region, binding to the antibody pair each of said analytes, producing a color change proportional to the each of analyte present from which a diagnosis of the cause of chest pain of a patient is made.

2. A method for rapidly diagnosing the cause of chest pain of a patient in the early onset thereof, said method comprising the steps of
   drawing a sample of serum or plasma from a patient,
   depositing the sample in a sample window of a diagnostic test kit, said test kit comprising
   a front panel comprising a sample window and a display window;
   a back panel; and
   a dry chemistry membrane affixed between the front and back panels positioned for display in at least the display window, wherein said membrane comprises:
   a sample region, and a control region, said sample region positioned to receive the sample from the sample window; and
   at least three antibody pairs located at discrete locations along said membrane between the sample region and the control region, each of said antibody pairs comprising an antibody reagent member and an immobilized capture antibody member, each capture antibody member being located on said membrane closer to the control region than the corresponding antibody reagent member, each antibody pair having a measurable or observable moiety labelled or chemically bonded to the antibody reagent member of each said antibody pairs,
   the antibody pairs being monoclonal or polyclonal and comprising:
   a first antibody pair that specifically binds to myoglobin,
   a second antibody pair that specifically binds to myosin light chains, and
   a third antibody pair that specifically binds to one protein selected from the group consisting of CK-MB, troponin I, and troponin T,
   such that upon adding sample to the sample window, analytes present in the sample and complementary to the antibody pairs will migrate toward the control region, binding to the antibody pair each of said analytes, producing a color change proportional to each concentration of analyte present,
   visualizing or measuring the moiety and diagnosing the cause of chest pain of a patient.

* * * * *